United States Patent [19]

Borom

[11] 4,237,559
[45] Dec. 9, 1980

[54] BONE IMPLANT EMBODYING A COMPOSITE HIGH AND LOW DENSITY FIRED CERAMIC CONSTRUCTION

[75] Inventor: Marcus P. Borom, Schenectady, N.Y.

[73] Assignee: General Electric Company, Schenectady, N.Y.

[21] Appl. No.: 38,097

[22] Filed: May 11, 1979

[51] Int. Cl.³ .............................................. A61F 1/03
[52] U.S. Cl. ...................................... 3/1.9; 128/92 C
[58] Field of Search ....................... 3/1.9, 1.91, 1.911, 3/1.912, 1.913; 433/201; 428/303, 304, 411; 128/92 C

[56] References Cited

U.S. PATENT DOCUMENTS

| | | | |
|---|---|---|---|
| 3,605,123 | 9/1971 | Hahn | 3/1.9 |
| 3,662,405 | 5/1972 | Bortz et al. | 3/1.9 |

FOREIGN PATENT DOCUMENTS

| | | | |
|---|---|---|---|
| 2447787 | 4/1976 | Fed. Rep. of Germany | 3/1.9 |
| 2755751 | 6/1978 | Fed. Rep. of Germany | 3/1.9 |

OTHER PUBLICATIONS

Driskell et al., "Development of Ceramic and Ceramic Composite Devices for Maxillofacial Applications", *J. Biomed. Mater. Res. Symposium*, pp. 345 and 353, 1972.

*Primary Examiner*—Clifford D. Crowder
*Attorney, Agent, or Firm*—Jane M. Binkowski; James C. Davis, Jr.; Leo I. MaLossi

[57] ABSTRACT

A composite high and low density fired ceramic article is employed as a bone implant. High density ceramic material forms the core or structural member of the composite. An integral inner portion of ceramic material having interconnected porosity encourages the growth of new bone marrow. An integral outer portion of porous ceramic material provides a means for bone and tissue attachment.

5 Claims, 1 Drawing Figure

U.S. Patent
Dec. 9, 1980
4,237,559
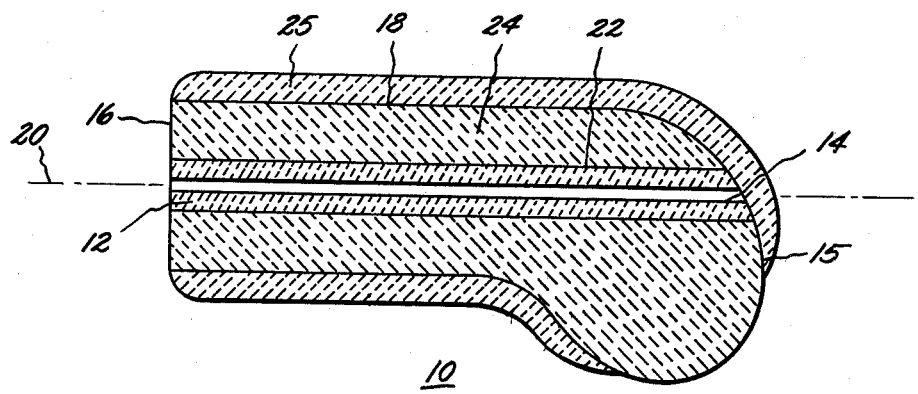

BONE IMPLANT EMBODYING A COMPOSITE HIGH AND LOW DENSITY FIRED CERAMIC CONSTRUCTION

BACKGROUND OF THE INVENTION

1. Field of Invention

This invention relates to bone implants and in particular to fired ceramic material embodying high and low density ceramic composite construction.

2. Description of the Prior Art

Surgically installed bone implants as replacements for bone sections, load bearing joints, roots of teeth and the like must be structurally sound, capable of knitting into existing bone structure and chemically compatible with body tissue and fluids. Bone knitting and tissue attachment to the implant is encouraged by employing structures containing sufficient, correctly sized porosity to provide a penetrable host for the infusion and growth of new tissue and bone material. Porous structures, however, do not always possess the load bearing strength required for structural implants.

Therefore, it is an object of this invention to provide a new and improved bond implant which overcomes at least some of the deficiencies of the prior art.

Another object of this invention is to provide a new and improved bone implant structure which is a composite fired ceramic article consisting of a three member structure.

Other objects of this invention will, in part, be obvious and will, in part, appear hereinafter.

BRIEF DESCRIPTION OF THE INVENTION

In accordance with the teachings of this invention there is provided a new and improved composite ceramic bore implant structure. The structure comprises a first ceramic member having an outer surface, opposed end surfaces and a central axis. Walls define an aperture which extends entirely through and terminates in the opposed end surfaces of the first member. The microstructure of the first member has a porosity content which is not greater than 20 percent by volume. Very little if any porosity is interconnected.

The first member functions principally as a strength bearing member as the structure becomes integral with the bone structure after implantation.

A second ceramic member is disposed within the aperture as well as encompassing the outer surface and possibly one end surface of the first member. The second member is integral with selected surface areas of the one end surface, the walls and the outer surface of the first member. The microstructure of the ceramic material of the second member after firing has a porosity content of from about 20 percent by volume to 65 percent by volume. The porosity is interconnected. The grain morphology is indicative of having undergone vapor transport action.

The portion of the material of the second member disposed in the aperture of the first member promotes bone knitting and bone marrow growth. The remainder of the material of the second member promotes bone knitting and tissue growth.

The material of each of the members is one selected from the group consisting of alumina, calcium aluminate, lanthanum aluminate and yttrium aluminate. Calcium aluminate is preferred because of the high calcium content in bone structures. The material may be the same in each member, or different from each other.

DESCRIPTION OF THE DRAWINGS

The FIGURE is a cross-sectional view of a fired composite ceramic bone implant.

DESCRIPTION OF THE INVENTION

With reference to the FIGURE there is shown an improved bone implant 10 embodying a composite of high and low density fired ceramic material. The implant comprises a first member 24 consisting of a fired ceramic material having a density of greater than 80 percent by volume. The member 24 consists of a ceramic material such, for example, as alumina, calcium aluminate, and the like. The grain size of the material before firing is from 0.5 micron to 45 microns. The member 24 has opposed end surfaces 15 and 16, an outer surface 18 and a longitudinal axis 20. The member 12 may be solid or preferably it may have walls 22 defining a longitudinal aperture which extends part way or all the way through the member 24 as shown in the FIGURE. The member 24 functions principally as a load bearing member of the implant.

The member 24, may be of any geometrical configuration and may be purchased, if economically feasible, or manufactured by suitable molding means such as by injection molding or slip casting.

A second member 25 of a fired ceramic material is formed about and is integral with a selected surface area of the walls 18 and at least a portion of one end surface 15 of the member 24. The material of the member 25 consists essentially of a ceramic material such, for example, as alumina, calcium aluminate, and the like.

The fired ceramic material is derived from a ceramic material composition embodying a reactant fugitive filler material. Preferably, the microstructure of the material of the member 25 will exhibit a porosity content of 40 percent by volume. The porosity content may range from about 30 percent by volume and up to 60 percent by volume. The porosity is interconnected and the grain morphology is characteristic of ceramic grains which have undergone vapor phase transport action. After firing the member 25 has a thickness which is dependent upon the end use of the bone implant.

The function of the member 25 is to provide a suitable means for enhancing bone knitting, to promote tissue growth and adherence of the same to the composite ceramic bone implant. A portion 12 of the member 25 which is formed within and is integral with the walls 22 of the member 24 functions to promote growth of bone marrow as well as to aid in bone knitting.

The preferred method of forming the member 25, as well as the members 12 and 24, in the unfired state is by injection molding or transfer molding. This preferred method enables one to design the structure of the composite bone implant 10 to be configured like the bone it is to replace.

In injection molding, the solids content of the material composition employed to form the members 25 and 12 when having a complex shape initially must be in excess of 50 percent by volume to prevent the solids included therein from becoming a discontinuous phase. Should the solid material become a discontinuous phase, upon binder removal and before sintering occurs, the member 25 may deform or disintegrate.

To increase porosity in the fired member 25 a reactant fugitive filler material is desirable. The reactant fugitive filler material provides, along with the ceramic material, the total solids content necessary for injection molding. Upon a subsequent firing at an elevated temperature, the reactant fugitive filler is reacted in a suitable manner to increase the porosity content of the member 25. A desirable reactant fugitive filler material is one which will also react with the ceramic material, for example alumina, to eliminate or remove a portion thereof from the member 25 and thereby increase the porosity content further. Suitable fugitive filler materials are those which will provide enough reactant material at the elevated temperature to reduce a portion of the ceramic material, i.e. alumina which, in part, is removed from the compact in the gaseous state and which, in part, is deposited on other alumina grains by vapor phase transport action causing coarsening and a rounding thereof. Preferred reactant bearing materials are graphite, aluminum, aluminum carbide, aluminum oxycarbide, boron and boron carbide. Suitable organic materials may also be employed as reactant materials as a carbon source.

The reactant fugitive filler material is usually a particular material mixed with the ceramic material. These two materials are the key ingredients for making the fired ceramic member 25. For injection molding purposes a plasticizing vehicle system is added. The plasticizing system is generally solely for making the material composition injection moldable for ease of fabrication with minimum work required and minimum wear on the tooling, including dies. Normally, the ingredients of the plasticizing systems are removable by melting or volatilization means before or during presintering operations whereas substantially all of the reactant fugitive filler material must be retained for the higher temperature processing relied upon to produce articles from the claimed material composition.

However, if a carbonaceous material could act as part of the plasticizing system, and if part or substantially all of it could furnish part or all of the required amount of reactant filler material in the claimed material composition, then such carbonaceous material is most desirable. Further, such carbonaceous material itself will chemically react with the alumina and other ceramic material in the same manner to produce the desired ceramic structure when the claimed material composition is utilized.

The reactant fugitive filler (Rff) material is present in the material composition to chemically react with the ceramic material and produce vapor phase suboxide species thereof which are then evolved in the vapor phase from the article during firing to achieve a desired level of porosity in the article. Some of the suboxide species is oxidized and redeposits on some of the ceramic grains producing some grain growth by vapor transport action. At the same time some densification may occur because of bulk diffusion but the dominating process is vapor transport which is initiated and continues to be carried out by the chemical reaction of the Rff material with the ceramic material. The Rff material and a portion of the ceramic material are used up chemically and evolve as a gas. The volume or space left void helps to produce the desired increase in porosity in the fired ceramic article.

The reactant fugitive filler material preferably has a particle size of the order of 300 microns or less. The particle size of the ceramic material, such as, alumina is important in that it helps control the size of the pores in the member 25. The particle size distribution of the ceramic material has a significant effect on the rheology of the wax-carbon-ceramic systems. The ceramic material should have an average particle size of 40 microns or less. The preferred average particle size range is from 1–20 microns.

When the ceramic material is alumina, such suitable alumina material is obtainable as fused alumina powder from the Norton Company. Suitable alumina powders are:

(a) Norton 38-900 Alundum wherein the particle size distribution is typically as follows:

| Particle Size | Weight Percentage |
|---|---|
| 0–5μ | 55.5 |
| 5μ–10μ | 34.0 |
| >10μ | remainder |

(b) Norton—500 mesh Alundum
(c) Norton—600 mesh Alundum Various blends of the flour powders may also be combined into a flour mixture.

One or more waxes can be employed to provide adequate deflocculation, stability and flow characteristics. The plasticizing vehicle system preferably consists of one or more paraffin type waxes which form the base material. A purified mineral wax, ceresin, may also be included in the base material. To 100 parts of the base wax material additions of oleic acid, which acts as a deflocculent, white beeswax, which acts as a deflocculent and aluminum stearate, which acts to increase the viscosity of the base wax, are added. A preferred plasticizing vehicle has the following composition:

| Binder | Material | Part by Weight | | |
|---|---|---|---|---|
| P-21 paraffin (Fisher Scientific) | | 33⅓ | | |
| P-22 paraffin (Fisher Scientific) | | 33⅓ | | |
| Ceresin (Fisher Scientific) | | 33⅓ | | |
| | Total | 100 parts | | |
| | | | Part by Weight | |
| Additives: | Material | Range | Preferred | Typical |
| | oleic acid | 0–12 | 6–8 | 8 |
| | beeswax, white | 0–12 | 3–5 | 4 |
| | aluminum stearate | 1–6 | 1–4 | 3 |

Despite the addition of defloculent, large particle size, of the order of >50μ, can settle at a rather rapid rate in the wax and change the sintering behavior of the remainder of the material mix of the molding composition material. The rate of settling of large particles is adjusted by varying the viscosity of the liquid medium, wax. To this end aluminum stearate is added to the wax to increase viscosity by gelling. Increased viscosity also has the additional benefits of preventing segregation of the wax and solids when pressure is applied and reducing the dilatancy of the material mixture.

In order to describe the invention more fully, and for no other reason, the ceramic material is said to be aluminum and the reactant fugitive filler material is said to be a carbon bearing material. The amount of carbon bearing material added to the core composition mix is dependent upon the porosity desired in the fired core as well as the average particle size of the alumina material. The carbon material present in the core material mix as graphite has a molar ratio of carbon to alumina G/A of $>0$ G/A$\leqq 1.25$. A preferred molar ratio range is $0.1 \leqq G/A \leqq 0.4$. This molar ratio range has been found to provide excellent results. Best results are achieved when $0.20 \leqq G/A \leqq 0.30$. The graphite is retained in the bisque ceramic during heating until the alumina begins to sinter and develops strength at the alumina-alumina particle contacts. The graphite can now be removed from the structure, or compact, without producing a discontinuous solid phase that could cause distortion of the compact.

The expected chemical reactions between alumina and carbon occur at temperatures greater than 1500° C. in a reducing or inert atmosphere. The result of these reactions is the production of volatile suboxides of alumina. The possible reactions are:

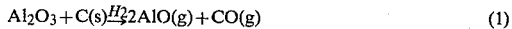

$$Al_2O_3 + C(s) \rightleftharpoons 2AlO(g) + CO(g) \quad (1)$$

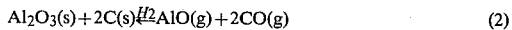

$$Al_2O_3(s) + 2C(s) \rightleftharpoons 2AlO(g) + 2CO(g) \quad (2)$$

with (2) being the most probable reaction to occur.

At temperatures above 1500° C., the vapor pressure of the suboxide is significant. As the vapor pressure increases, mass transport by an evaporation-condensation type mechanism can occur. If the rate of mass transport through the vapor phase is much greater than mass transport by volume or grain boundary diffusion, the material is merely rearranged in the compact and little or no reduction in the pore volume (i.e. densification) can take place. In the reducing or inert atmosphere, the suboxide can escape thereby lowering the density of the members 12 and 25 or fired ceramic and producing the microstructure described heretofore.

The effect of carbon additions, in the form of graphite, on the weight loss of the ceramic article when fired in a reducing atmosphere, such as hydrogen, is a function of atmosphere and consequently heating rate above about 900° C.

When the heating rate is less than the order of about 100° C. per hour in the temperature range of from about 900° C. to about 1500° C., with oxygen present as an impurity in the controlled atmosphere, the expected porosity content is not obtained. Apparently, the carbon reacts with the gaseous oxygen impurity to form gaseous CO and $CO_2$, which escapes from the compact. Consequently, insufficient carbon is available above about 1500° C. to reduce the alumina to a gaseous suboxide and produce the fired compact of desired porosity content. With the material composition described and in the controlled atmosphere to be discussed, the heating rate practiced is of the order of 300° C./hour up to 1800° C. However, the most practical method of preventing oxidation of carbon is by proper atmosphere control.

Controlled atmospheres for firing the compact and to obtain the desired chemical reactions in the remaining material may be of a reducing type or of an inert gas type having an extremely low oxygen content. Hydrogen may be employed as a reducing gas type atmosphere. Argon, helium, neon and the like may be utilized for atmospheres of the inert gas type.

The effects of carbon additions on the linear shrinkage of the fired ceramic is dependent upon the molar ratio of carbon to alumina, the amount of oxygen impurity in the atmosphere, and the heating rate.

As the molar ratio of carbon to alumina is increased the percent linear shrinkage of the compact is decreased. The molar ratio of carbon to alumina may be inadvertently reduced in the compact during the firing if oxygen impurities in the atmosphere react with a portion of the carbon in the compact to form CO or $CO_2$. When a slow heating rate is lowered by oxidation of carbon and high shrinkages result. When a fast heating rate is used the carbon to alumina ratio is not greatly affected by oxidation of carbon and low shrinkages result. If the firing atmospheres were completely free of any oxygen or water vapor the resulting linear shrinkage would be independent of the heating rate used and would only be a function of the initial carbon content. For example, when the carbon to alumina ratio is about 0.75, the linear shrinkage is only 2% if a fast heating rate is practiced when the controlled atmosphere includes the presence of oxygen as an impurity therein. In contrast, under the same conditions, with a slow heating rate, a linear shrinkage as high as 13% has been observed. A low shrinkage is desirable in preventing porous ceramic 25 from cracking and/or separating from dense ceramic 24. The integrity of the structure of the implant 10 must be retained until the body has sufficient time to grow new bone structure and body tissues making the implant 10 an integral part of the body structure which has been mended.

The percent linear shrinkage is also dependent on the grain size of the alumina flour employed. A larger grain size material will decrease the percent linear shrinkage which will occur. Therefore, as stated previously, the grain size of the ceramic(alumina) flour employed in making the fired member 25 is preferably from about 1 micron to about 40 microns.

Although the molar ratio of carbon (with the carbon expressed as graphite) to alumina affects the various physical characteristics of the fired ceramic articles, the rate of heating concomitant with the oxygen partial pressure also has a pronounced effect on the fired articles. Therefore, an improperly fired ceramic article has less porosity, i.e. is more dense and undergoes higher shrinkage.

The percent weight loss due to the loss of carbon and/or alumina is dependent upon the firing temperature. Above about 1550° C., the loss becomes appreciable and is related to molar ratio of carbon to alumina. The greater effect is noted when the molar ratio is of the order of 0.75 and above.

The molar ratio of graphite to alumina, G/A affects the fired density of ceramic articles made from the material composition mix for making the members 12 and 25. For molar ratios $0.25 < G/A < 0.75$, the fired density increases slightly with increasing temperature up to about 1500° C. Above 1500° C., the higher molar ratio materials show a significant decrease in the fired density of the ceramic article.

The following teachings of this invention reveal the effects of the dewpoint of the hydrogen gas. Equivalent partial pressures of the oxygen in inert gases can also be employed to form the desired structure of the fired compacts. However, for purposes of illustration only, and for no other reason, the invention is further described employing hydrogen gas having a given dewpoint range.

In order to maintain continuous porosity in the member 25 and also achieve the desirable microstructure of the same, the member 25 is fired at the elevated temperature of about 1500° C. and upwards in an atmosphere of controlled dewpoint hydrogen gas. The hydrogen gas has a dewpoint of less than $-35°$ F. Preferably, the dewpoint of the hydrogen gas should be $-80°$ F. or lower. The dryer the gas, the more the gas is suitable for the firing process. Suitable inert gases are argon, helium, neon and the like containing the desired partial pressure of oxygen.

The dewpoint should not exceed −35° F. (∼200 ppm water) and is preferred to be less than −80° F.(∼8 ppm water) since the compact undergoes less of a weight loss with increasing dewpoint values. This may occur as a result of the following reaction between water contained in the hydrogen gas and the reactant fugitive material carbon $$H_2O + C \rightarrow CO \uparrow + H_2 \uparrow \tag{3}$$

wherein an increase in the amount of $H_2O$ available for reacting with the carbon causes the compact to lose greater amounts of carbon through oxidation.

The low dewpoint gases are preferred since porosity of members 12 and 25 increases with decreasing dewpoint.

The member has interconnected porosity which comprises from 20 to 65 percent by volume. The firing temperature has a range of from 1650° C. to about 1900° C. with a preferred range of from about 1750° C. to about 1850° C. The compact is fired in this range for a period of from about 15 minutes to about 4 hours.

Other suitable alumina starting materials may include rare earth doped alumina wherein the alumina is in excess and the reactant fugitive filler material will reduce the excess alumina present. Such materials include yttrium aluminate and lanthanum aluminate. Calcium aluminate is desirable because of the presence of calcium in the material bone structure.

The material composition of this invention when prepared for injection molding may be prepared in several ways. A preferred method embodies the use of the Sigma mixer having a steam jacket for heating the contents. When the plasticizer material is comprised of one or more waxes, the wax is placed in the mixer and heated to a temperature of from 80° C. to 110° C. to melt the wax or waxes. The additive agents of one or more defloculents and aluminum stearate are then added, as required, in the desired quantities. The mixing is continued for about 15 minutes to assure a good mixture of the ingredients. The desired quantity of reactant fugitive filler material is then added and mixing, at the elevated temperature, is continued until all visible chunks of reactant fugitive filler material are broken up. To this mixture is then added the alumina bearing flour or mixture of flours of the desired size distribution. Mixing is then continued, in vacuum, at the elevated temperature for about 30 minutes or until the flour materials are universally distributed throughout the mixture. The heat is turned off and coolant water passed through the steam jacket to cool the mixture. Mixing is continued for a period of from 30 to 40 minutes, or until the mix is pelletized to a desired size of less than 2 cm.

Employing the composition mix one is able to injection mold complex shaped articles 12 and 25 in and around the high density ceramic structural member of the composite bone prosthesis 10 at from 200 psi to 10,000 psi and upwards to 50,000 psi at temperatures of from 80° C. to 130° C. The shrinkage of such composition mix is on the order of about 1 percent by volume.

The wax is removed from the injected member 25 by heating the member 10 to a temperature of less than 1100° C. to remove the organic binder. For example, the compact is heated to a temperature of several hundred degrees Celsius until the wax or plasticizer material drains from the member 25. Preferably, member 10 comprising the injected member 25 is placed in high surface area carbon flour having a pore size less than the pore size of the injected member 25 after wax removal. This enables the wax to be withdrawn by a capillary action induced by the finer pore size packing material. Other suitable packing materials are activated charcoal, high surface area carbon black and activated alumina. The wax, as described heretofore, is almost completely removed from the injected molded member 25 at about 200° C. Subsequent heat treatment is used to sinter the material of the member 25 to increase its mechanical strength.

The firing schedule entails a partial removal of the wax from the member 25 by heating the member 25 at less than 25° C./hr to a temperature of no greater than 200° C. in packing material. The wax remaining is only of the order of from 2% by weight to 4% by weight. The member 25 is then removed from the packing powder and placed in the sintering furnace. The wax still remaining in the member 25 gives the member 25 good handling strength. A heating rate of less than 25° C. per hour is employed up to about 400° C. to remove the remainder of the wax. In order to avoid any oxidation of the reactant fugitive filler material, the subsequent heating rate should be as rapid as possible. The member 25 is thereafter heated at a rate greater than 200° C. per hour, preferably about 300° C. per hour, up to 1650° C. or higher, even up to the order of 1800° C. Upon reaching this predetermined elevated temperature, isothermal heating is practiced for a sufficient time for the reactant fugitive filler material to react with the alumina present to produce the desired level of porosity in the member 25. A preferred isothermal heating cycle is approximately 2 hours. Other heating schedules may be employed as long as care is taken to prevent oxidation of carbon and the subsequent higher shrinkage of the member 24.

Gaseous suboxides of alumina are formed in a reducing atmosphere above about 1500° C. to form the desired porous microstructure of the member 25. A portion of aluminum suboxides which are not redeposited on grains escape from the member 25 into the furnace atmosphere.

It is significant to note that when the gases of the controlled atmosphere are completely free of oxygen or water vapor, the heating rate is of little or no importance.

When the fugitive reactant material is either aluminum or boron, the probable chemical reactions between alumina and aluminum and boron, include the following:

$$Al_2O_3 + 4Al \rightarrow 3Al_2O \tag{4}$$

$$Al_2O_3 + Al \rightarrow 3AlO \tag{5}$$

$$Al_2O_3 + 2B \rightarrow Al_2O + 2BO \tag{6}$$

$$Al_2O_3 + B \rightarrow 2AlO + BO \tag{7}$$

For a more detailed description of material compositions embodying reactant fugitive filler materials one is directed to copending patent application Ser. No. 6279 filed Jan. 25, 1979 now U.S. Pat. No. 4,184,885 entitled "An Aluminum Core Having A High Degree of Porosity And Crushability Characteristics" of Wayne D. Pasco and Frederic J. Klug which is assigned to the same assignee of this invention.

The composite member 10 may be held in place in the bone structure by surgical screws and/or pins until sufficient bone and tissue growth occurs to integrate the composite implant into the bone structure.

I claim as my invention:

1. A composite ceramic bone implant structure comprising a first ceramic member having an outer surface, opposed end surfaces, a central axis and walls defining an aperture which extends entirely through said member and terminates in the opposed end surface;

the first member consists essentially of a fired ceramic material which is one selected from the group consisting of alumina, calcium aluminate, lanthanum aluminate and yttrium aluminate;

the microstructure of the ceramic material of the first member has a porosity content which is no greater than 20 percent by volume;

a second ceramic member disposed within the aperture, encompassing, and integral with selected surface areas of the outer surface, and the walls of the first ceramic member;

the second ceramic member consists essentially of a fired ceramic material which is one selected from the group consisting of alumina, calcium aluminate, lanthanum aluminate and yttrium aluminate, and the microstructure of the fired ceramic material of the second member has a porosity content of from about 20 percent by volume to 65 percent by volume, at least a portion of the porosity being interconnected and the grain morphology is indicative of having undergone vapor transport action.

2. The composite bone implant structure of claim 1 wherein the ceramic material of each member is calcium aluminate.

3. The composite bone implant structure of claim 1 wherein the porosity of the first member is not interconnected.

4. The composite bone implant structure of either claim 1, 2 or 3 wherein the second ceramic member encompasses and is integral with selected surface areas of at least one end surface.

5. The composite bone implant structure of claim 4 wherein the ceramic material of the first and second member is alumina.

* * * * *